United States Patent [19]

Shepherd

[11] 4,245,120

[45] Jan. 13, 1981

[54] 4-(MONOALKYLAMINO)BENZENE POLYCARBOXYLIC ACIDS

[75] Inventor: Robert G. Shepherd, South Nyack, N.Y.

[73] Assignee: American Cyanamid Company, Stamford, Conn.

[21] Appl. No.: 836,945

[22] Filed: Sep. 27, 1977

[51] Int. Cl.³ .............................................. C07C 101/66
[52] U.S. Cl. ..................................... 562/458; 560/19; 560/49; 560/50; 546/261; 546/262; 546/264; 260/501.11; 260/501.2; 424/309; 424/319; 424/263
[58] Field of Search ........... 260/518 R, 501.11, 501.2; 560/19, 49, 50; 562/458; 546/264, 262, 261; 424/309, 319

[56] References Cited

U.S. PATENT DOCUMENTS

| | | | |
|---|---|---|---|
| 2,597,965 | 5/1952 | Adams | 260/518 R |
| 3,758,561 | 9/1973 | Rogers et al. | 260/518 R |
| 3,803,211 | 4/1974 | Dolejs et al. | 562/458 |
| 3,868,416 | 2/1975 | Albright et al. | 260/518 R |

FOREIGN PATENT DOCUMENTS

766609 1/1957 United Kingdom ................ 260/518 R

OTHER PUBLICATIONS

Parker et al., J. Med. Chem., vol. 20 (6), pp. 781–786 (1977).

*Primary Examiner*—James H. Reamer
*Attorney, Agent, or Firm*—Edward A. Conroy, Jr.

[57] ABSTRACT

This disclosure describes the monoalkylaminobenzene multi-carboxylic acids, derivatives and salts thereof useful as hypolipidemic and anti-atherosclerotic agents.

17 Claims, No Drawings

4-(MONOALKYLAMINO)BENZENE POLYCARBOXYLIC ACIDS

BRIEF SUMMARY OF THE INVENTION

This invention relates to new organic compounds, and more particularly is concerned with monoalkylaminobenzene multi-carboxylic acids, derivatives and salts thereof, which may be represented by the following structural formula:

wherein $R_1$ is a straight chain or branched alkyl group of the formula $C_nH_{2n+1}$ wherein n is an integer from 8 to 19, inclusive; $R_2$ is hydrogen or a group convertible in vivo thereinto such as methyl, ethyl, carboxymethyl, lower alkanoyl ($C_1$-$C_6$), succinyl, 1-(sodium sulfo)-lower alkyl, 1-(sodium sulfo)polyhydroxyalkyl or 1,3-bis(sodium sulfo)aralkyl; m is 2 or 3; and $R_3$ is selected from the group consisting of hydrogen, alkyl having up to 4 carbon atoms, carboxyalkyl, mono- or di-hydroxyalkyl, dialkylaminohydroxyalkyl, polymethyleneiminohydroxyalkyl, phenyl, halophenyl, carboxyphenyl, benzyl, halobenzyl, carboxybenzyl, pyridylmethyl, halopyridylmethyl, carboxypyridylmethyl, 3-pyridyl, halo-3-pyridyl, carboxy-3-pyridyl, alkali metal cations and alkaline earth metal cations.

A preferred embodiment of this invention consists of those compounds in which the monoalkylaminobenzene moiety bears 3,4-, 3,5- or 3,4,5-polycarboxylic substitution, either in the free or derivatized state, and the pharmaceutically acceptable salts thereof, namely those of the formula:

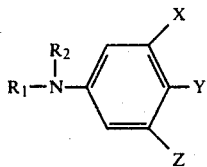

wherein $R_1$ and $R_2$ are as previously defined and X, Y, and Z are each individually selected from the group consisting of hydrogen, and —$COOR_3$ with the proviso that at any one time only one of these three substituent may be hydrogen.

The straight chain alkyl groups for the substituent $R_1$ may be, for example, octyl nonyl, decyl, undecyl, dodecyl, tridecyl, tetradecyl, pentadecyl, hexadecyl, heptadecyl, octadecyl, and nonadecyl. Suitable branched alkyl groups for the substituent $R_1$ may be for example, 1-methylpentadecyl, 1-ethyltetradecyl, 1-heptylnonyl, 2-ethyldodecyl, 1,4-diethyloctyl, 11-methyldodecyl, 5,5-dimethylhexyl, 4,8,12-trimethyltridecyl, 2,4,6,8-tetramethylnonyl, 1,4-dimethyl-1-ethylhexyl, 15-methylhexadecyl, 13,13-dimethyltetradecyl, 15,15-dimethylhexadecyl, and the like.

The invention also pertains to novel compositions of matter useful as antiatherosclerotic agents and to methods of meliorating atherosclerosis by counteracting hyperlipemia and arterial plaque formation in mammals therewith; the active ingredients of said compositions of matter being the novel 4-(monoalkylamino)phenyl carboxylic acids of the present invention as the free acids or in the derivatized form or in the form of a pharmaceutically acceptable salt with an organic or inorganic acid or base. The invention also contemplates a method for lowering serum lipids and for meliorating atherosclerosis in mammals by the administration of said acids.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in their initiation and development and also, most importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon & Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson & Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine and nicotinic acid [(Levy & Fredererickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Orally active agents are required since patients usually take them for a number of years.

DETAILED DESCRIPTION OF THE INVENTION

U.S. Pat. No. 3,868,416 discloses and claims certain 4-monoalkylaminobenzoic acids, esters, pharmaceutically acceptable salts, pharmaceutical compositions thereof and a method of lowering serum lipid levels in mammals therewith. No prior art is known which discloses monoalkylaminobenzene multi-carboxylic acids and derivatives and salts thereof of this invention and no hypolipidemic activity has been reported in the literature for these compounds and they are different in structure from other hypolipidemic agents. The compounds of this invention lower serum-lipid concentrations and also minimize atheroma formation in the aorta. These monoalkylaminobenzene multi-carboxylic acids provide the oral administration required of hypolipidemic agents, which patients usually take for many years. The anti-atherogenic activity of alkylaminobenzoic acids has been announced; Abstract No. 27, American Oil Chemists Society, 67th Meeting, New Orleans, Apr. 21-24, 1976; Federation Proceedings 36, Abstract No. 4706 (1977).

We have now found that members of this class of compounds can safely and effectively lower serum lipids in warm-blooded animals. For some time it has been considered desirable to lower serum lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm blooded mammals for the treatment of hyperlipidemic and atherosclerotic states found in patients with or prone to heart attacks, to peripheral or cerebral vascular disease, and to stroke.

The monoalkylaminobenzene multi-carboxylic acids of the present invention are, in general, crystalline solids having characteristic melting points and spectral characteristics. They are soluble in organic solvents such as lower alkanols, chloroform, benzene, dimethylformamide, and the like, but are generally insoluble in water.

The novel compounds of the present invention form non-toxic acid-addition salts with a variety of pharmacologically acceptable inorganic salt-forming reagents. Thus, acid-addition salts, resulting from admixture with excess of the acid in a neutral solvent, are formed with such acids as sulfuric, phosphoric, hydrochloric, hydrobromic, and the like. The acid-addition salts of the organic bases of the present invention are, in general, crystalline solids. The carboxylic acid salts may be either of inorganic salt-forming cations, such as the alkali metals, sodium, potassium, lithium; the alkaline earth metals, calcium, magnesium, and the like; ammonia, or of an organic nature, such as salts with ethyl amine, diethylamine, diethanolamine, pyridine, triethylamine, etc.

The compounds of the invention can generally be prepared as follows. Reaction of 5-amino-1,2,3-benzenetricarboxylic acid triphenyl ester with a bromoalkane in an organic solvent such as hexamethylphosphoramide at a temperature of 90°–150° C. for 8–24 hours produces the 5-alkylamino-1,2,3-benzenetricarboxylic acid triphenyl ester as oils. Similarly, from dimethyl 5-aminoisophthalate there are obtained the dimethyl 5-alkylaminoisophthalates as white crystalline solids which may be recrystallized from an organic solvent pair such as methylene chloride-petroleum ether (b.p. 30°–65° C.). Also from diethyl 4-aminophthalate there are obtained the white crystalline diethyl 4-alkylaminophthalates, which may be recrystallized from an organic solvent pair such as methylene chloride-petroleum ether (b.p. 30°–65° C.).

These alkylaminobenzene multi-carboxylic acids and esters are also prepared by alkylations employing other alkylhalides, sulfates, tosylates or mesylates with or without solvent at 50°–150° C. using an excess of the aminobenzene multi-carboxylic ester as base or an equivalent of an organic or inorganic base. Other methods of preparation are (a) reductive alkylation of the aminobenzene multi-carboxylic acids or esters with suitable carbonylalkanes, and (b) diborane reduction of alkanoylaminobenzene multi-carboxylic acids or esters. These reactions may also be carried out on aminobenzene polynitriles to produce alkylaminobenzene polynitriles which are then hydrolyzed to the corresponding carboxylic acids or are alcoholyzed to the esters.

Saponification with aqueous alcoholic solution of potassium hydroxide at ambient to reflux temperature for 1 to 24 hours generate the 5-alkylamino-1,2,3-benzenetricarboxylic acids, 5-alkylaminoisophthalic acids, and the 4-alkylaminophthalic acids. These multi-carboxylic acids are crystalline compounds and have definite melting points. Treatment of these multi-carboxylic acids with sodium hydroxide in aqueous alcoholic solutions result in the sodium salts which are generally collected by filtration from the reaction mixture. Other alkali metal and alkali earth metal salts may be similarly prepared. Treatment with ammonium hydroxide produces the ammonium salts, whereas various organic amines give the organic amine salt, such as the triethanolamine salt.

The mineral acid salts may be conveniently prepared by treatment at 0°–30° C. of the amine compounds of the invention with hydrogen chloride, hydrogen bromide, sulfuric acid and the like in a solvent such as diethyl ether, tetrahydrofuran, dimethoxyethane, and collecting the salt therefrom.

The N-alkanoyl derivatives may be prepared by treatment of the amine moiety of the compounds of the invention in pyridine with an acylating agent such as acetic anhydride at a temperature of 20°–100° C. for a period of 1–24 hours. Addition of ice-water precipitates the desired N-alkanoyl compounds which are crystalline products with definite melting points.

Certain derivatives

of the aminobenzoyl nitrogen atom are useful for providing greater solubility, more uniform and reliable intestinal absorption, and for a certain degree of modification of the pharmacology of the compounds of the present invention. Some of these derivatives can be converted to the corresponding N-H forms by the acidity of the stomach or the alkalinity of the small intestine. Others are converted by metabolic processes. The methyl and carboxymethyl derivatives and the like are prepared by the alkylation, reductive alkylation, and acylamino reduction methods above. Derivatives such as the acetyl and succinyl compounds may be prepared using acetyl chloride, acetic anhydride, succinic anhydride, etc. in the presence of pyridine, triethylamine or the like at temperatures moderate enough to avoid acylation of the amide moiety. The 1-(sodium sulfo)alkyl derivatives are obtained by reaction of the 4-(monoalkylamino)benzamides, or suitable intermediates in certain cases, with sodium bisulfite and an aliphatic aldehyde, a polyhydroxyaldehyde such as glyceraldehyde or glucose, or cinnamaldehyde, in a mixed organic-aqueous medium. In the case of cinnamaldehyde, the di-sulfonate salts result from addition of the bisulfite to the carbon-nitrogen double bond of the anil intermediate as well as to the carbon-carbon of cinnamaldehyde itself.

The novel compounds of the present invention are not only hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered conveniently by the oral route. It is not known how these novel compounds operate in the blood serum and no theory of why these compounds so operate is advanced. It is not intended that the present invention should be limited to any particular mechanism of action of lowering serum lipids or of meliorating atherosclerosis, or be limited to compounds actng by only one mechanism.

The compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: A binder such as gum tragacanth, acacia, corn starch or gelatin; excipients such as dicalcium phosphate,; a disintegrating agent such as corn starch, potato starch, alginic acid, and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active ingredients may be incorporated into sustained-release preparations and formulations.

The invention will be described in greater detail in conjunction with the following examples.

EXAMPLE 1

5-Nitro-1,2,3-benzenetricarboxylic acid

To a stirred mixture of 125 g. of 1,2,3-benzenetricarboxylic acid and 900 ml. of concentrated sulfuric acid at 60°–70° C. is added, gradually over a 2 hour period, 312 g. of potassium nitrate. The mixture is heated at 135°–140° C. for 16 hours, cooled and treated with ice and water. Some solid is separated out and is dissolved in water. The entire aqueous mixture is extracted with ether, the extract is washed with water and dried over magnesium sulfate. The ether is concentrated to a small volume, and petroleum ether is added to precipitate a white solid. The solid is collected and dried to give 76.5 g. of the product of the Example.

EXAMPLE 2

5-Nitro-1,2,3-benzenetricarbonyl chloride

5-Nitro-1,2,3-benzenetricarboxylic acid, 300 ml. of thionyl chloride and 2.0 ml. of dimethylformamide is heated under reflux for 16 hours. The solvent is evaporated in vacuo and the residue is dissolved in chloroform. The chloroform is concentrated to a small volume, and the residue is dissolved in carbon tetrachloride. On standing, a yellow solid is separated, collected and dried to give 30.0 g. of material. A mixture of this material with 100 ml. of thionyl chloride and 2.0 ml. of dimethylformamide is refluxed for 16 hours. The solvent is evaporated and the resulting yellow solid is crystallized from chloroform:carbon tetrachloride to give 23.0 g. of the product of the Example.

EXAMPLE 3

5-Nitro-1,2,3-benzenetricarboxylic acid Triphenyl Ester

To a stirred solution of 30.6 g. of phenol in 100 ml. of pyridine (dried over molecular sieves) is added 22.7 g. of 5-nitro-1,2,3-benzenetricarbonyl chloride. The solution is heated on a steam bath for one hour, cooled and poured into 500 ml of cold water with vigorous stirring resulting in the separation of a solid. The mixture is filtered, and the solid is washed with water to give a brown powder. The product is dissolved in 100 ml. of methylene chloride and filtered. The filtrate is boiled on a steam bath and 250 ml. of ethanol is added portionwise to the boiling solution until all of the methylene chloride has been removed. The mixture is cooled to room temperature, and the product formed is separated, washed with ethanol and ether, then is dissolved in 75.0 ml. of methylene chloride. It is then recrystallized from 200 ml. of ethanol as above, separated and dried to yield 30.8 g. of the subject triphenyl ester.

EXAMPLE 4

5-Amino-1,2,3-benzenetricarboxylic acid Triphenyl Ester

A solution of 29.0 g. of 5-nitro-1,2,3-benzenetricarboxylic acid triphenyl ester in dimethylformamide is hydrogenated on a Parr shaker in the presence of 10% palladium-on-carbon catalyst. The mixture is filtered through diatomaceous earth and the filtrate is diluted with water and extracted with methylene chloride. The extract is dried over anhydrous sodium sulfate and evaporated to give an oil. The oil is crystallized from ether, and the solid is recrystallized from benzene and twice from ethanol to provide 15.0 g of the product of the Example.

EXAMPLE 5

5-Hexadecylamino-1,2,3-benzenetricarboxylic acid Triphenyl Ester

A stirred mixture of 16.07 g. of 5-amino-1,2,3-benzenetricarboxylic acid triphenyl ester and 5.4 g. of 1-bromohexadecane in 30 ml. of hexamethylphosphoramide is heated at 125°–130° C. (oil-bath) for 22 hours. The cooled solution is poured into water, and an oil separates. The supernatant is decanted, and the gum is dissolved in methylene chloride. The organic phase is separated from any water, dried over anhydrous sodium sulfate and evaporated. The residual oil is purified by adsorption chromatography on a silica gel column and eluted with methylene chloride to give a light yellow oil as the product of the Example.

Similarly, 1-bromooctane, 1-bromononane, 1-bromodecane, 1-bromoundecane, 2-bromododecane, 1-bromododecane, 1-bromotridecane, 1-bromotetradecane, 1-bromopentadecane, 1-bromo-14-methylpentadecane, 1-bromoheptadecane, 1-bromooctadecane, and 1-bromononadecane, give respectively, 5-octylamino-1,2,3-benzenetricarboxylic acid triphenyl ester, 5-nonylamino-1,2,3-benzenetricarboxylic acid triphenyl ester, 5-decylamino-1,2,3-benzenetricarboxylic acid triphenyl ester, 5-undecylamino-1,2,3-benzenetricarboxylic acid triphenyl ester, 5-(1-methylundecyl)amino-1,2,3-benzenetricarboxylic acid triphenyl ester, 5-dodecyclamino-1,2,3-benzenetricarboxylic acid triphenyl ester, 5-tridecylamino-1,2,3-benzenetricarboxylic acid triphenyl ester, 5-tetradecylamino-1,2,3-benzenetricarboxylic acid triphenyl ester, 5-pentadecylamino-1,2,3-benzenetricarboxylic acid triphenyl ester, 5-(14-methylpentadecyl)amino-1,2,3-benzenetricarboxylic acid triphenyl ester, 5-heptadecylamino-1,2,3-benzenetricarboxylic acid triphenyl ester, 5-octadecylamino-1,2,3-benzenetricarboxylic acid triphenyl ester, and 5-nonadecylamino-1,2,3-benzenetricarboxylic acid triphenyl ester.

EXAMPLE 6

5-Hexadecylamino-1,2,3-benzenetricarboxylic acid

A stirred mixture of 9.1 g. of 5-hexadecylamino-1,2,3-benzenetricarboxylic acid triphenyl ester, 7.4 g. of potassium hydroxide in 100 ml. of ethanol and 10 ml. of water is heated at reflux temperature for 2.5 hours. The resulting solution is diluted with 70 ml. of water, and concentrated to remove ethanol, and then is acidified with 17 ml. of concentrated hydrochloric acid. The solution is diluted with 400 ml. of water to precipitate solid which is collected by filtration. The solid is recrystallized from ether-petroleum ether (b.p. 30°–65° C.) to yield 5.4 g. of white solid, m.p. 126°–129° C., the product of the Example.

The product of the Example in tetrahydrofuran is treated with hydrogen chloride gas for 3 minutes and the precipitated hydrochloride salt is collected by filtration.

Similarly, the 5-alkylamino-1,2,3-benzenetricarboxylic acid triphenyl esters described in Example 5 give, respectively, 5-octylamino-1,2,3-benzenetricarboxylic acid, 5-nonylamino-1,2,3-benzenetricarboxylic acid, 5-decylamino-1,2,3-benzenetricarboxylic acid, 5-undecylamino-1,2,3-benzenetricarboxylic acid, 5-(1-methylundecyl)amino-1,2,3-benzenetricarboxylic acid, 5-dodecylamino-1,2,3-benzenetricarboxylic acid, 5-tridecylamino-1,2,3-benzenetricarboxylic acid, 5-tetradecylamino-1,2,3-benzenetricarboxylic acid, 5-pentadecylamino-1,2,3-benzenetricarboxylic acid, 5-(14-methylpentadecyl)amino-1,2,3-benzenetricarboxylic acid, 5-heptadecylamino-1,2,3-benzenetricarboxylic acid, 5-octadecylamino-1,2,3-benzenetricarboxylic acid, and 5-nonadecylamino-1,2,3-benzenetricarboxylic acid.

EXAMPLE 7

5-Hexadecylamino-1,2,3-benzenetricarboxylic acid Trisodium Salt

A magnetically stirred mixture of 5.28 g. of 5-hexadecylamino-1,2,3-benzenetricarboxylic acid and 1.42 g. of sodium hydroxide in 60 ml. of ethanol-water (9:1) is stirred at room temperature for 3 hours. The mixture is filtered, and the solid is washed successively with ethanol and diethyl ether to yield 5.2 g. of the product as a white solid.

Similarly, the 5-alkylamino-1,2,3-benzenetricarboxylic acids described in Example 6 give, respectively, 5-octylamino-1,2,3-benzenetricarboxylic acid trisodium salt, 5-nonylamino-1,2,3-benzenetricarboxylic acid trisodium salt, 5-decylamino-1,2,3-benzenetricarboxylic acid trisodium salt, 5-undecylamino-1,2,3-benzenetricarboxylic acid trisodium salt, 5-(1-methylundecyl)amino-1,2,3-benzenetricarboxylic acid trisodium salt, 5-dodecylamino-1,2,3-benzenetricarboxylic acid trisodium salt, 5-tridecylamino-1,2,3-benzenetricarboxylic acid trisodium salt, 5-tetradecylamino-1,2,3-benzenetricarboxylic acid trisodium salt, 5-pentadecylamino-1,2,3-benzenetricarboxylic acid trisodium salt, 5-(14-methylpentadecyl)amino-1,2,3-benzenetricarboxylic acid trisodium salt, 5-heptadecylamino-1,2,3-benzenetricarboxylic acid trisodium salt, 5-octadecylamino-1,2,3-benzenetricarboxylic acid trisodium salt, and 5-nonadecylamino-1,2,3-benzenetricarboxylic acid trisodium salt.

EXAMPLE 8

Dimethyl 5-Hexadecylaminoisophthalate

In the manner described in Example 5, treatment of 23.4 g. of dimethyl 5-aminoisophthalate with 17.1 g. of 1-bromohexadecane in 70 ml. of hexamethylphosphoramide produces white crystals, m.p. 90°–91° C. after recrystallization from methylene chloride-petroleum ether (b.p. 30°–65° C.).

Similarly, 1-bromooctane, 1-bromononane, 1-bromodecane, 1-bromoundecane, 1-bromododecane, 2-bromododecane, 1-bromotridecane, 1-bromotetradecane, 1-bromopentadecane, 1-bromo-14-methylpentadecane, 1-bromoheptadecane, 1-bromooctadecane, and 1-bromononadecane gave respectively, dimethyl 5-octylaminoisophthalate, dimethyl 5-nonylaminoisophthalate, dimethyl 5-decylaminoisophthalate, dimethyl 5-undecylaminoisophthalate, dimethyl 5-dodecylaminoisophthalate, dimethyl 5-(1-methylundecylamino)isophthalate, dimethyl 5-tridecylaminoisophthalate, dimethyl 5-tetradecylaminoisophthalate, dimethyl 5-pentadecylaminoisophthalate, dimethyl 5(14-methylpentadecyl)aminoisophthalate, dimethyl 5-heptadecylaminoisophthalate, dimethyl 5-octadecylaminoisophthalate, and dimethyl 5-nonadecylaminoisophthalate.

EXAMPLE 9

5-Hexadecylaminoisophthalic acid

In the manner described in Example 6, treatment of 6 g. of dimethyl 5-hexadecylaminoisophthalate with 6 g. of potassium hydroxide in 80 ml. of ethanol and 8 ml. of water produces white crystals, m.p. 153°–156° C. after recrystallization from acetone-petroleum ether (b.p. 30°–65° C.).

Similarly, the dimethyl alkylaminoisophthalates in Example 8 provide: 5-octylaminoisophthalic acid, 5-nonylaminoisophthalic acid, 5-decylaminoisophthalic acid, 5-undecylaminoisophthalic acid, 5-dodecylaminoisophthalic acid, 5-(1-methylundecyl)aminoisophthalic acid, 5-tridecylaminoisophthalic acid, 5-tetradecylaminoisophthalic acid, 5-pentadecylaminoisophthalic acid, 5-(14-methylpentadecyl)aminoisophthalic acid, 5-heptadecylaminoisophthalic acid, 5-octadecylaminoisophthalic acid, and 5-nonadecylaminoisophthalic acid.

EXAMPLE 10

5-Hexadecylaminoisophthalic acid Disodium Salt

In the manner described in Example 7, treatment of 5.12 g. of 5-hexadecylaminoisophthalic acid with 1.01 g. of sodium hydroxide in 50 ml. of water is productive of the disodium salt, the product of the Example.

Similarly, the alkylaminoisophthalic acids in Example 9 provide: 5-octylaminoisophthalic acid disodium salt, 5-nonylaminoisophthalic acid disodium salt, 5-decylaminoisophthalic acid disodium salt, 5-undecylaminoisophthalic acid disodium salt, 5-dodecylaminoisophthalic acid disodium salt, 5-(1-methylundecylamino)isophthalic acid disodium salt, 5-tridecylaminoisophthalic acid disodium salt, 5-tetradecylaminoisophthalic acid disodium salt, 5-pentadecylaminoisophthalic acid disodium salt, 5-(14-methylpentadecyl)aminoisophthalic acid disodium salt, 5-heptadecylaminoisophthalic acid disodium salt, 5-octadecylaminoisophthalic acid disodium salt, and 5-nonadecylaminoisophthalic acid disodium salt.

EXAMPLE 11

Diethyl 4-hexadecylaminophthalate and Diethyl N-acetyl 4-hexadecylaminophthalate In the manner described in Example 5, treatment of 17.65 g. of diethyl 4-aminophthalate with 11.35 g. of 1-bromohexadecane in 50 ml. of hexamethylphosphoramide produces white crystals, m.p. 59°–60° C., after recrystallization from methylene chloride-petroleum ether (b.p. 30°–65° C.).

The product of the Example (150 mg.) in pyridine (1 ml.) is treated with acetic anhydride (0.5 ml.), and the mixture is allowed to stand at room temperature for 3 hours, and poured into cold-water. The crystals of diethyl 4-N-hexadecylacetamidophthalate are collected and washed with water.

Similarly, 1-bromooctane, 1-bromononane, 1-bromodecane, 1-bromoundecane, 2-bromododecane, 1-bromododecane, 1-bromotridecane, 1-bromotetradecane, 1-bromopentadecane, 1-bromo-14-methylpentadecane, 1-bromoheptadecane, 1-bromooctadecane, and 1-bromononadecane give, respectively, diethyl 4-octylaminophthalate, diethyl 4-nonylaminophthalate, diethyl 4-decylaminophthalate, diethyl 4-undecylaminophthalate, diethyl 4-(1-methylundecyl)aminophthalate, diethyl 4-dodecyl aminophthalate, diethyl 4-tridecylaminophthalate, diethyl 4-tetradecylaminophthalate, diethyl 4-pentadecylaminophthalate, diethyl 4-(14-methylpentadecyl)aminophthalate, diethyl 4-heptadecylaminophthalate, diethyl 4-octadecylaminophthalate, and diethyl 4-nonadecylaminophthalate.

EXAMPLE 12

4-Hexadecylaminophthalic acid

In the manner described in Example 6, treatment of 8.5 g. of diethyl 4-hexadecylaminophthalate with 7.5 g. of potassium hydroxide in 100 ml. of ethanol and 10 ml. of water produces white crystals, m.p. 134°–136° C., after recrystallization from ether-petroleum ether (b.p. 30°–65° C.).

Similarly, the diethyl 4-alkylaminophthalates described in Example 11 give, respectively, 4-octylaminophthalic acid, 4-nonylaminophthalic acid, 4-decylaminophthalic acid, 4-undecylaminophthalic acid, 4-(methylundecyl)aminophthalic acid, 4-dodecylaminophthalic acid, 4-tridecylaminophthalic acid, 4-tetradecylaminophthalic acid, 4-pentadecylaminophthalic acid, 4-(14-methylpentadecyl)aminophthalic acid, 4-hepadecylaminophthalic acid, 4-octadecylaminophthalic acid, and 4-nonadecylaminophthalic acid.

EXAMPLE 13

4-Hexadecylaminophthalic acid Disodium Salt

In the manner described in Example 7, treatment of 6.86 g. of 4-hexadecylaminophthalic acid with 1.37 g. of sodium hydroxide in 50 ml. of water produces the disodium salt.

Similarly, the 4-alkylaminophthalic acids described in Example 12 give, respectively, 4-octylaminophthalic acid disodium salt, 4-nonylaminophthalic acid disodium salt, 4-decylaminophthalic acid disodium salt, 4-undecylaminophthalic acid disodium salt, 4-(1- methylundecyl)aminophthalic acid disodium sodium salt, 4-dodecylaminophthalic acid disodium salt, 4-tridecylaminophthalic acid disodium salt, 4-tetradecylaminophthalic acid disodium salt, 4-pentadecylaminophthalic acid disodium salt, 4-(14-methylpentadecyl)aminophthalic acid disodium salt, 4-heptadecylaminophaltic acid disodium salt, 4-octadecylaminophthalic acid disodium salt, and 4-nonadecylaminophthalic acid disodium salt.

EXAMPLE 14

1-Bromo-14-methylpentadecane

A solution of 3-methylbutylmagnesiumbromide is prepared by treating 15.1 g. of 3-methylbutylbromide with 2.7 g. of magnesium turnings in 50 ml. of dry tetrahydrofuran. The resultant Grignard reagent is added dropwise to a solution of 34.5 g. of 1,11-dibromoundecane and 0.2 g. of lithium copper chloride in 75 ml. of tetrahydrofuran. After standing for one hour at $-10°$ C., the solution is evaporated and the resultant oil is distilled in vacuo to yield the colorless product of the Example.

EXAMPLE 15

| Preparation of 50 mg. tablets | | |
|---|---|---|
| Per Tablet | | Per 10,000 Tablets |
| 0.050 gm. | Active ingredient | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | | 15 gm. |
| 0.150 gm. | | 1490 gm. |

The active ingredient, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 16

| Preparation of Oral Suspension | |
|---|---|
| Ingredient | Amount |
| Active Ingredient | 500 mg. |
| Sorbitol solution (70% N.F.) | 40 ml. |
| Sodium Benzoate | 150 mg. |
| Saccharin | 10 mg. |
| Red dye | 10 mg. |
| Cherry flavor | 50 mg. |
| Distilled water qs ad | 100 ml. |

The sorbitol solution is added to 40 ml. of distilled water and the active ingredient is suspended therein. The saccharin, sodium benzoate, flavor and dye are added and dissolved. The volume is adjusted to 100 ml. with distilled water. Each ml. of syrup contains 5 mg. of active ingredient.

EXAMPLE 17

Dimethyl 5-(hexadecylamino)isophthalate

A solution of 50.5 g. of 5-(hexadecylamino)isophthalic acid and 34.4 ml of boron trifluoride etherate in 200 ml. of methanol is stirred under reflux for 44 hours, allowed to cool, and is poured into 1.20 liters of ice cold 5% aqueous sodium carbonate solution. The white solid is collected by filtration and recrystallized from benzene-ethanol to yield white crystalline ester, m.p. 90°–91° C.

EXAMPLE 18

2,3-Dihydroxypropyl 4-(hexadecylamino)phthalate

A solution of 7.34 g. of 4-(hexadecylamino)phthalic acid, 9.6 g. of 25% aqueous sodium hydroxide, and 12.6 g. of 3-iodo-1,2-propanediol in 50 ml. of hexamethylphosphoramide is stirred for 24 hours at ambient temperature, diluted with 100 ml. of ether and stirred for 5 days at ambient temperature. The mixture is treated with water and extracted with ether. The dried extracts are evaporated to yield the white crystalline 1-glyceryl ester of 4-(hexadecylamino)phthalic acid.

I claim:

1. A compound selected from the group consisting of those of the structural formula:

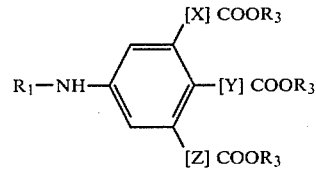

wherein $R_1$ is, a straight chain or branched alkyl group of the formula $C_nH_{2n+1}$ wherein n is an integer from 8 to 19, inclusive and $R_3$ is selected from the group consisting of hydrogen, alkyl having up to 4 carbon atoms, carboxylalkyl, mono- or dihydroxyalkyl, dialkylaminohydroxyyalkyl polymethyleneiminohydroxyalkyl, phenyl, halophenyl, carboxyphenyl, benzyl, halobenzyl, carboxybenzyl, pyridmethyl, halopyridylmethyl, carboxypridylmethyl, 3-pyridyl, halo-3-pyridyl, carboxy-3-pyridyl, alkali metal cations and alkali earth metal cations and the pharmaceutically acceptable acid addition salts thereof.

2. A compound selected from the group consisting of those of the structural formula:

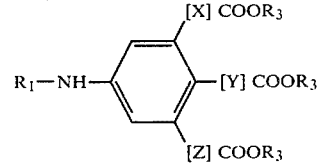

wherein $R_1$ is a straight chain or branched alkyl group of the formula $C_nH_{2n+1}$ wherein n is an integer from 8 to 19 inclusive; $R_3$ is selected from the group consisting of hydrogen, alkali metal cations and alkali earth metal cations, and the pharmaceutically acceptable acid addition salts thereof.

3. A compound selected from the group consisting of those of the formula:

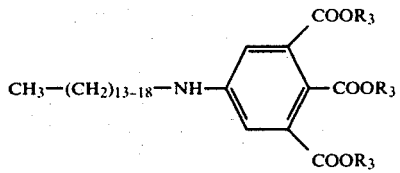

wherein R₃ is as defined in claim 2.

4. A compound selected from the group consisting of those of the structural formula:

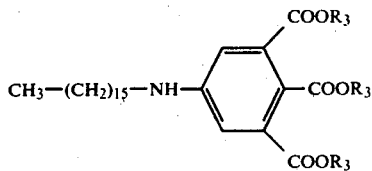

wherein R₃ is as defined in claim 1.

5. A compound selected from the group consisting of those of the structural formula:

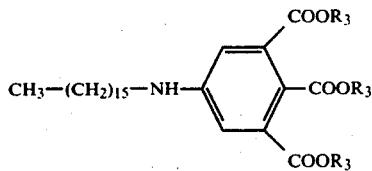

wherein R₃ is as defined in claim 2.

6. A compound selected from the group consisting of those of the structural formula:

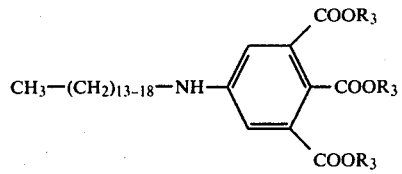

wherein R₃ is as defined in claim 1.
7. 5-Tetradecylamino-1,2,3-benzenetricarboxylic acid.
8. 5-Pentadecylamino-1,2,3-benzenetricarboxylic acid.
9. 5-(14-Methylpentadecyl)amino-1,2,3-benzenetricaboxylic acid.
10. 5-Hexadecylamino-1,2,3-benzenetricarboxylic acid.
11. 5-Heptadecylamino-1,2,3-benzenetricarboxylic acid.
12. 5-Octadecylamino-1,2,3-benzenetricarboxylic acid.
13. 5-Nonadecylamino-1,2,3-benzenetricarboxylic acid.
14. 5-Pentadecylamino-1,2,3-benzenetricarboxylic acid.
15. 5-(14-Methylpentadecyl)amino-1,2,3-benzenetricarboxylic acid.
16. 5-Hexadecylamino-1,2,3-benzenetricarboxylic acid trisodium salt.
17. 5-(14-Methylpentadecyl)amino-1,2,3-benzenetricarboxylic acid trisodium salt.

* * * * *